United States Patent [19]

Keogh

[11] Patent Number: 5,429,618

[45] Date of Patent: Jul. 4, 1995

[54] THROMBORESISTANT ARTICLES

[75] Inventor: James R. Keogh, Maplewood, Minn.

[73] Assignee: Medtronic, Inc., Minneapolis, Minn.

[21] Appl. No.: 212,333

[22] Filed: Mar. 14, 1994

Related U.S. Application Data

[62] Division of Ser. No. 969,636, Oct. 30, 1992, abandoned.

[51] Int. Cl.$^6$ .................................................. A61M 5/32
[52] U.S. Cl. .................................... 604/266; 623/12; 424/78.17
[58] Field of Search ............... 623/1, 11, 12; 604/93, 604/264–266; 424/78; 427/36

[56] References Cited

U.S. PATENT DOCUMENTS

| | | | |
|---|---|---|---|
| 4,459,318 | 7/1984 | Hyans | 427/36 |
| 4,872,867 | 10/1989 | Joh | 604/269 |
| 5,004,461 | 4/1991 | Wilson | 604/265 |
| 5,019,601 | 5/1991 | Allen | 523/122 |

FOREIGN PATENT DOCUMENTS 1320068 12/1989 Japan.

OTHER PUBLICATIONS

Kishida et al. "Cell Behavior on polymeric surfaces grafted with non-ionic and ionic monomers" *Biomaterials*, vol. 12, Oct. 1991.

"The Search for Thromboresistance Using Immobilized Heparin" by Larsson et al., in Blood in Contact with Natural and Artificial Surfaces, Annals of the New York Academy of Sciences, vol. 516, 1987.

"Modification of Material Surfaces to Affect How they Interact with Blood", by Allan S. Hoffman in Blood in Contact with Natural and Artificial Surfaces, Annuls of the New York Academy of Sciences, vol. 516, 1987.

"Interrelation of Protein Adsorption and Blood Compatibility of Biomaterials", by Sevastianov in High Performance Biomaterials, Technomic Publishing Co., Inc. pp. 313–341, 1991.

Primary Examiner—C. Fred Rosenbaum
Assistant Examiner—Chalin Smith
Attorney, Agent, or Firm—Daniel W. Latham; Harold R. Patton

[57] ABSTRACT

Articles comprised of 2-acrylamido-2-methyl propane sulfonic acid (AMPS) polymer on a blood-contacting substrate or the like are useful in medical devices in which antithrombogenic characteristics and slippery surfaces are required.

12 Claims, 1 Drawing Sheet

THROMBORESISTANT ARTICLES

This is a divisional of application Ser. No. 07/969,636 filed on Oct. 30, 1992, now abandoned.

BACKGROUND OF THE INVENTION

For over forty years a number of medical devices which contact the blood or blood product of living persons or animals have been developed, manufactured and used clinically. A partial list of such articles would include pacemakers, arterial grafts, heart valves, artificial hearts, heart pumps, hip protheses, heart lung machines, catheters and kidney dialysis equipment.

A major problem with such articles is that their working surfaces, (i.e., surfaces which contact blood or blood products), are foreign to those substances and tend to initiate, among other things, red blood cell destruction and coagulation to form clots (thrombogenesis).

Normal intact endothelium is nonthrombogenic due partly to the synthesis of heparan sulfate. Heparan sulfate tends to remain bound to the surface of endothelial cells accelerating the inactivation of thrombin, the enzyme responsible for the polymerization of fibrinogen to fibrin in clot formation, by anti thrombin III (ATIII). Heparan sulfate is a very powerful anticoagulant in the natural vasculature. Heparin is a strongly acidic glycosaminoglycan. It has a high content of N- and O-sulfonate groups and carboxylic groups. Heparin is structurally similar to heparan sulfate although it is more sulfated. The anticoagulant activity of heparin is directly dependant on its molecular size and electric charge. Thus, increasing the molecular weight and/or the amount of sulfonation will increase the anticoagulant activity. Therefore, it is felt that a highly sulfonated polymer surface may stimulate the inhibition of thrombin by ATIII. Consequently, it has been of great interest to physicians and the medical industry to devise blood-contacting polymeric surfaces that possess characteristics of heparan sulfate, specifically by coating surfaces with heparin. For example, in U.S. Pat. No. 3,826,678 to Hoffman et al., biologically active molecules are chemically bonded to polymers and copolymers which previously have been radiation-grafted to inert polymeric substrates such as polyurethane and polyethylene. The grafted polymer is preferably a hydrophilic hydrogel e.g., hydroxyethyl methacrylate (HEMA) and may include heparin bonded to the hydrogel.

BRIEF DESCRIPTION OF THE INVENTION

We have discovered new and improved thromboresistant articles in which thromboresistant slip coatings of polymerized 2-acrylamido-2-methyl propane sulfonic acid (AMPS) are provided on the working surfaces of articles of the type herein contemplated to fight thrombosis while providing slippery surfaces on the article surface. The invention is particularly useful for articles employing surfaces of polyurethane and other polymers. The invention therefore comprises a thromboresistant article for use in contact with blood or blood products which has a body formed with an exposed surface for contacting blood or blood products in which the surface has been provided with a polymerized AMPS. The polymerized AMPS my be provided by a polymeric article surface which has grafted to it a graft polymerized AMPS, a pre-polymerized AMPS dip coated onto the article surface, or pre-polymerized AMPS incorporated into the polymer used for the article surface.

DETAILED DESCRIPTION OF THE INVENTION

Figure 1:
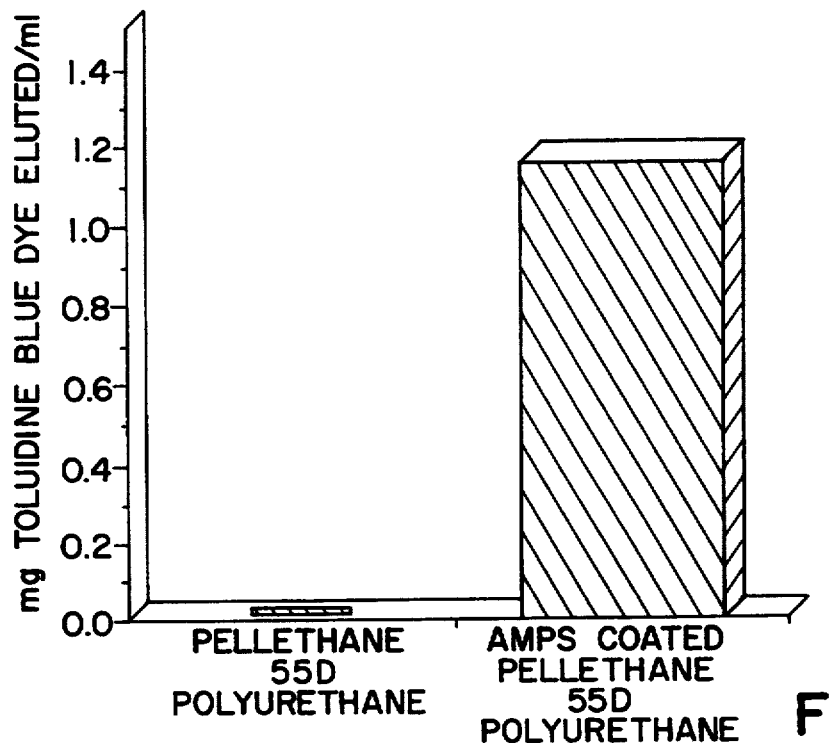
FIG. 1 is a graph showing the amount of toluidine blue dye released from the surfaces of Pellethane 55D polyurethane and Pellethane 55D polyurethane grafted with AMPS.

The kinds of articles contemplated by this invention may be provided by articles which incorporate at least on outer surfaces thereof at least in part a solid-phase substrate. Preferably the substrate is a polymeric substrate of the type listed in the group of materials shown in Table 1.

TABLE 1

Polyamides
Polycarbonates
Polyethers
Polyesters
Polyolefins
Polystyrene
Polyurethane
Poly(ether urethane)
Polyvinyl chlorides
Silicones
Polyethylenes
Polypropylenes
Polyisoprenes
Polytetrafluorethylenes At the present time it is believed that polyurethane sometimes referred to as poly(ether urethane) provides the preferred polymeric substrate. The kinds of articles contemplated by this invention are therefore preferably provided with polyurethane substrates and are intended to contact blood or blood products.

The slippery, thromboresistant polymer to be used originates with a monomer of AMPS. By "AMPS" herein we mean 2-acrylamido-2-methyl propane sulfonic acid and salts of the acid such as the sodium salt. Such a monomer creates a hydrophilic polymer when polymerized. A hydrophilic surface minimizes protein interactions and also provides slip properties to the surface. These monomers contain a vinyl group. Such groups are necessary for free radical polymerization to occur.

Specifically, a number of graft slip coatings of AMPS, dip coatings of pre-polymerized AMPS and AMPS/polymer blends have been prepared and used according to this invention. The most preferred are comprised of monomers individually grafted onto the substrate surface via ceric ion initiation (Ce IV).

While ceric ion initiation (Ce IV) is presently most preferred as the technique to be used to graft these monomers to polyurethane and other polymeric substrate surfaces, according to this invention other grafting techniques are well known and may be used in appropriate situations. For example, corona discharge, UV irradiation and ionizing radiation ($^{60}$Co, X-rays, high energy electrons, plasma gas discharge) are known. These grafting techniques are examples of how to form free radicals on a polymer substrate working surface. The free radicals formed thereon initiate the grafting of vinyl ($CH_2=CH-R$) type monomers as required to form the graft polymerized AMPS coating required by this invention.

Although the detailed discussion below mentions examples in which treatment is on polyurethane films as the polymeric substrate surface and article, it is not intended that this invention be so limited. Antithrombogenic coatings of AMPS may be similarly bound to other polyurethane article substrate surfaces, i.e., surface any articles intended to contact blood or blood products. The invention contemplates articles of any shape or form including tubular, sheet, rod and articles of proper shape for use in artificial organs, blood handling equipment or bodily implants of any kind and to any encapsulant means therefore wherein polymeric, preferably polyurethane, surfaces are involved.

AMPS THROMBORESISTANT COATING

The grafted AMPS coating is aimed at producing a surface that will decrease the nonspecific adsorption of various proteins due to its hydrophilicity and provide a highly sulfonated surface that will preferentially adsorb ATIII. The technique developed is based on the generation of free radicals on a polyurethane surface with Ce IV ion and the graft copolymerization of AMPS monomers directly to that surface.

EXAMPLE I

Extruded Pellethane 55D polyurethane was used, as the polyurethane material. It was obtained from the Dow Chemical Company of Midland, Mich. 48640. Films of the material were extracted in acetone for 72 hours and ethanol for another 72 hours prior to Ce IV ion grafting. The solvent extraction process removes any processing aids that might interfere with the grafting process. A 50% AMPS monomer solution in DI water was prepared and 20 ml of Ce IV ion solution per 100 ml of monomer solution was added. The Ce IV ion solution consisted of 2.74 g ceric ammonium nitrate and 3.15 g nitric acid in 50 ml DI water. The Ce IV-monomer solution was then degassed and released to nitrogen prior to grafting. Pellethane samples were placed into the degassed monomer solutions and stirred. Grafting was allowed to proceed for 2 hours. Grafted samples were then removed and thoroughly washed in DI water.

The presence of sulfonic acid groups on AMPS grafted material was measured using toluidine blue dye. Being positively charged, toluidine blue dye will ionically associate with negatively charged surfaces. Therefore, the binding of toluidine blue dye to the AMPS surface indicates the presence of negative charges due to the sulfonic acid groups in AMPS. AMPS grafted samples were therefore placed into a 1% toluidine blue dye/DI water solution for 1 minute and then rinsed in DI water. The bound dye was then released from the surface using a 1% SDS (sodium dodecyl sulfate) solution. The amount of dye eluted was determined spectrophotometrically at 640 nm. The amount of dye released from plain untreated Pellethane 55D polyurethane samples and Pellethane 55D polyurethane samples grafted with AMPS is shown in FIG. 1.

As the results indicate Pellethane 55D polyurethane containing no AMPS adsorbed no toluidine blue dye. This is due to the fact that Pellethane 55D polyurethane contains no negatively charged groups. However, the AMPS coating adsorbed a large amount of toluidine blue dye indicating the presence of sulfonic acid groups on the surface. As the AMPS surface contained a large amount of sulfonation, its ability to bind ATIII was investigated next.

EXAMPLE 2

Figure 2:
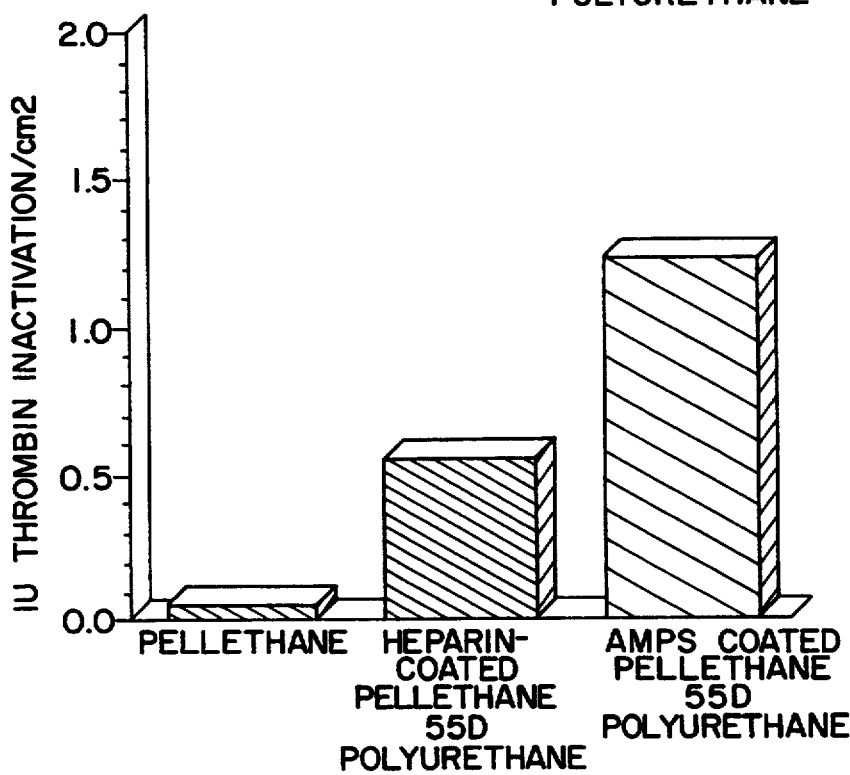
FIG. 2 is a graph showing a comparison of ATIII activity of Pellethane 55D polyurethane, heparin-coated Pellethane 55D polyurethane and AMPS grafted onto Pellethane 55D polyurethane samples. The results are expressed as the amount of thrombin inactivated by the sample (surface/cm$^2$).

Since clotting may be retarded on AMPS surface coated materials by the activation of ATIII by the sulfonic acid groups present on the modified polymer substrate surface, the surface-mediated activation of ATIII by AMPS coated samples was assessed. Samples were first rinsed in PBS (phosphate buffered saline solution) for 15 minutes prior to ATIII exposure. Following rinsing, the samples were exposed for 15 minutes to an excess of purified ATIII (50 IU/ml). Non-adsorbed ATIII was removed by rapid rinsing in tris-buffered saline, pH 7.4 at 25° C. (100 mM NaCl and 50 mM tris). The amount of surface bound and activated ATIII was then estimated by incubating the samples with an excess of thrombin. After a 10 minute incubation with constant mixing at 25° C., the residual thrombin was measured by reaction with a chromogenic substrate (H-D-phenylalanyl-L-pipecolyl-L-arginine-p-nitroanilide dichloride) in a spectrophotometer. The change in absorbance at 405 nm was then measured. The results are given in FIG. 2. As the results demonstrate, the AMPS coated surface appears to have heparin-like activity. In fact, the AMPS coated samples exhibit more ATIII activity than heparin-coated polyurethane samples. The heparin coating used was CBAS ® (Carmeda ® Bioactive Surface), a heparin coating available from Carmeda AB, a Swedish Company. This heparin-like effect is due to the sulfonic acid groups present in the AMPS coating. Grafted AMPS coatings therefore possess nonthrombogenic properties usually associated with heparin-coated materials.

EXAMPLE 3

The pre-polymerization of AMPS monomer.

Procedure: Mix 25.0 g AMPS monomer with 25.0 g DI water, pull a vacuum on the mixture and release nitrogen gas. While stirring under a blanket of nitrogen gas, add:

1 ml $K_2S_2O_5$ (3.78 g/100 ml water)
1 ml $K_2S_2O_8$ (3.76 g/100 ml water)
1 ml $FeSO_4 7H_2O$ (0.24 g/100 ml water)

Continue to stir, maintaining the nitrogen blanket until the mixture polymerizes. Upon polymerization, place the resultant gel in 50° C. vacuum oven overnight for drying. After drying, remove the dried gel and place in a micro-mill and mill the gel into a powder.

EXAMPLE 4

Blending of AMPS polymer into polyurethane substrate.

Procedure: Mix together the following and stir the mixture until the polymers have completely dissolved.

0.8 g AMPS polymer from Example 3
4.1 g polyurethane
120.0 g DMAC
1.0 g DI water Pour into films and let dry in a 50° C. vacuum oven overnight.

EXAMPLE 5

Dip coating of AMPS polymer onto a polyurethane substrate.

Procedure: Mix together the following and stir the mixture until the AMPS polymer dissolves completely.

0.3 g AMPS polymer from Example 3
50.0 g DMAC
0.3 g DI water Dip polyurethane films into the AMPS polymer solution for 5 seconds, remove and dry.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated. Those skilled in the art may recognize other equivalents to the specific embodiment described herein which equivalents are intended to be encompassed by the claims attached hereto.

What is claimed is:

1. A method for reducing thrombosis when an article is used in contact with blood or blood products, the method comprising: providing an article having at least one exposed surface for contacting blood, applying to the surface an antithrombogentic agent of polymerized 2-acrylamido-2-methyl propane sulfonic acid (AMPS) polymer and placing the coated surface into contact with blood.

2. The method of claim 1 in which the exposed surface provided on the article is a polymeric surface.

3. The method of claim 2 in which the AMPS polymer is applied by graft polymerization onto the polymeric surface.

4. The method of claim 2 in which the AMPS polymer is blended applied by blending it into the polymeric surface.

5. The method of claim 2 in which the polymeric surface is polyurethane.

6. The method of claim 1 in which the AMPS polymer is applied by dip coating onto the article surface.

7. The method of claim 1 in which the article is placed into contact with blood by implantation in a human or animal body.

8. The method of claim 1 in which the article is placed into contact with blood or blood products by flowing blood through the article.

9. The article of claim 1 in which the article is a temporary indwelling device.

10. A method for reducing thrombosis for an implantable article comprising the steps of:
    (a) preparing an aqueous solution of 2-acrylamido-2-methylpropane sulfonic acid monomer and Ce IV ion;
    (b) contacting a polymeric, blood-contacting surface of the implantable article with the monomer solution for a period of time effective to provide a polymer of 2-acrylamido-2-methylpropane sulfonic acid grafted to the surface; and
    (c) implanting the article in the living body of a person or an animal with the grafted surface of the article in blood contact.

11. A method for reducing thrombosis for an implantable article comprising the steps of:
    (a) polymerizing 2-acrylamido-2-methylpropane sulfonic acid monomer;
    (b) dissolving the polymerized monomer in a solvent which is also capable of dissolving a polyurethane polymer;
    (c) combining the polymerized monomer solution with a polyurethane polymer;
    (d) forming the combined polymerized monomer and polyurethane polymer into a blood-contacting surface for the implantable article; and
    (e) implanting the article and blood-contacting surface in the living body of a person or an animal with the blood-contacting surface of the article in blood contact.

12. A method for reducing thrombosis for an implantable article comprising the steps of:
    (a) polymerizing 2-acrylamido-2-methylpropane sulfonic acid monomer;
    (b) dissolving the polymerized monomer in a solvent which is also capable of dissolving a polyurethane polymer;
    (c) applying the polymerized monomer solution to a blood-contacting polyurethane surface of the implantable article; and
    (d) implanting the article and blood-contacting surface in the living body of a person or an animal with the blood-contacting surface of the article in blood contact.

* * * * *